(12) United States Patent
Thibault et al.

(10) Patent No.: US 6,904,662 B2
(45) Date of Patent: Jun. 14, 2005

(54) METHOD OF SEALING A CARTRIDGE OR OTHER MEDICAL CONTAINER WITH A PLASTIC CLOSURE

(75) Inventors: Jean-Claude Thibault, Saint Egreve (FR); Hubert Jansen, Marburg-Michelbach (DE); Volker Niermann, Little Falls, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 465 days.

(21) Appl. No.: 09/841,371

(22) Filed: Apr. 24, 2001

(65) Prior Publication Data

US 2003/0177629 A1 Sep. 25, 2003

Related U.S. Application Data

(63) Continuation-in-part of application No. 09/732,538, filed on Dec. 8, 2000, now Pat. No. 6,681,475, and a continuation-in-part of application No. 09/421,657, filed on Oct. 20, 1999, now abandoned, which is a continuation-in-part of application No. 09/168,502, filed on Oct. 8, 1998, now Pat. No. 6,382,442.
(60) Provisional application No. 60/082,372, filed on Apr. 20, 1998.

(51) Int. Cl.[7] .............................................. B23P 11/00
(52) U.S. Cl. ............................ 29/511; 29/513; 29/450; 215/249; 215/247; 215/327; 604/411; 604/403
(58) Field of Search ............................... 29/511, 505, 510, 29/508; 215/249, 247, 327, 324; 604/411, 403, 405

(56) References Cited

U.S. PATENT DOCUMENTS

| | | | |
|---|---|---|---|
| 37,221 A | 12/1862 | Dunton | |
| 659,519 A | 10/1900 | De Oliveria | |
| 2,342,215 A | 2/1944 | Perelson | |
| 2,388,634 A | 11/1945 | De Woody | |
| 2,409,788 A | * 10/1946 | Osborne | ....................... 53/488 |
| 2,524,365 A | 10/1950 | Smith | |
| 2,607,503 A | 8/1952 | Sonnenberg | |
| 2,653,609 A | 9/1953 | Smith | |
| 2,659,370 A | 11/1953 | Smith | |
| 2,665,023 A | * 1/1954 | Migneault | ................... 215/272 |
| 2,667,986 A | 2/1954 | Perelson | |
| 2,953,132 A | 3/1960 | Richter et al. | |

(Continued)

*Primary Examiner*—David P. Bryant
*Assistant Examiner*—Stephen Kenny
(74) *Attorney, Agent, or Firm*—David M. Fortunato

(57) ABSTRACT

A method of sealing a cartridge having a barrel with a polymeric closure, wherein the polymeric closure includes a tubular collar portion and an integral radial portion, The method includes disposing the tubular collar portion over the radial rim portion of the barrel to surround the reduced diameter neck portion and incrementally rolling and radially deforming the tubular collar portion adjacent its free end into the reduced diameter neck portion with a crimping tool, wherein the polymeric closure is sufficiently malleable to permit radial deformation, yet sufficiently rigid and resistant to creep to retain its shape following deformation The crimping tool or tools include an inclined surface having a gradually decreasing angles of inclination which are driven against the tubular collar portion adjacent the free end and the cartridge assembly and crimping tool are relatively rotated.

22 Claims, 4 Drawing Sheets

U.S. PATENT DOCUMENTS

| | | |
|---|---|---|
| 3,033,202 A | 5/1962 | Richter et al. |
| 3,164,303 A | 1/1965 | Trautmann |
| 3,206,080 A | 9/1965 | Scislowicz |
| 3,243,070 A * | 3/1966 | Hoyle .................... 215/326 |
| 3,278,063 A | 10/1966 | Kranzhoff |
| 3,356,093 A | 12/1967 | Monahon |
| 3,357,427 A | 12/1967 | Wittke et al. |
| 3,610,297 A | 10/1971 | Raaf et al. |
| 3,674,028 A | 7/1972 | Ogle |
| 3,779,371 A | 12/1973 | Rovinksi |
| 3,810,469 A | 5/1974 | Hurschman |
| 3,826,260 A | 7/1974 | Killinger |
| 3,838,689 A | 10/1974 | Cohen |
| 3,872,992 A | 3/1975 | Larson |
| 3,940,003 A | 2/1976 | Larson |
| 3,977,555 A | 8/1976 | Larson |
| 3,995,630 A | 12/1976 | van de Veerdonk |
| 4,020,839 A | 5/1977 | Klapp |
| 4,048,999 A | 9/1977 | Kobel |
| 4,067,440 A | 1/1978 | Lataix |
| 4,153,057 A | 5/1979 | Kobel |
| 4,187,893 A | 2/1980 | Bujan |
| 4,210,255 A | 7/1980 | Pan |
| 4,296,786 A | 10/1981 | Brignola |
| 4,336,891 A | 6/1982 | Smith |
| 4,387,879 A | 6/1983 | Tauschinski |
| 4,412,623 A | 11/1983 | Schmidt |
| 4,418,827 A | 12/1983 | Butterfield |
| 4,425,120 A | 1/1984 | Sampson et al. |
| 4,460,735 A | 7/1984 | Froix |
| 4,462,502 A * | 7/1984 | Luenser .................... 215/329 |
| 4,493,348 A | 1/1985 | Lemmons |
| 4,505,709 A | 3/1985 | Froning et al. |
| 4,507,113 A | 3/1985 | Dunlap |
| 4,564,054 A | 1/1986 | Gustavsson |
| 4,573,506 A | 3/1986 | Paoletti |
| 4,573,976 A | 3/1986 | Sampson et al. |
| 4,576,211 A | 3/1986 | Valentini et al. |
| 4,588,403 A | 5/1986 | Weiss et al. |
| 4,619,651 A | 10/1986 | Kopfer et al. |
| 4,624,393 A | 11/1986 | Lopez |
| 4,639,250 A | 1/1987 | Rycroft |
| 4,662,878 A | 5/1987 | Lindmayer |
| 4,672,996 A | 6/1987 | Floyd et al. |
| 4,673,404 A | 6/1987 | Gustavsson |
| 4,675,020 A | 6/1987 | McPhee |
| 4,699,286 A * | 10/1987 | Nolan .................... 215/256 |
| 4,792,053 A | 12/1988 | Towns et al. |
| 4,822,351 A | 4/1989 | Purcell |
| 4,826,491 A | 5/1989 | Schramm |
| 4,834,149 A | 5/1989 | Fournier et al. |
| 4,834,152 A | 5/1989 | Howson et al. |
| 4,850,994 A | 7/1989 | Zerbet et al. |
| 4,884,703 A | 12/1989 | O'Meara |
| 4,909,290 A | 3/1990 | Coccia |
| 4,913,945 A | 4/1990 | Maruhashi et al. |
| 4,923,447 A | 5/1990 | Morgan |
| 4,927,423 A | 5/1990 | Malmborg |
| 4,932,937 A | 6/1990 | Gustavsson et al. |
| 4,982,740 A | 1/1991 | Broden |
| 5,006,118 A | 4/1991 | Yule |
| 5,024,256 A | 6/1991 | Vadjer |
| 5,035,689 A | 7/1991 | Schroeder |
| 5,060,812 A | 10/1991 | Ogle, II |
| 5,088,996 A | 2/1992 | Kopfer et al. |
| 5,092,840 A | 3/1992 | Healy |
| 5,116,326 A | 5/1992 | Schmidt |
| 5,169,385 A | 12/1992 | Turnbull |
| 5,171,214 A | 12/1992 | Kolber et al. |
| 5,215,538 A | 6/1993 | Larkin |
| 5,217,433 A | 6/1993 | Bunin |
| 5,232,029 A | 8/1993 | Knox et al. |
| 5,232,109 A | 8/1993 | Tirrell et al. |
| 5,250,037 A | 10/1993 | Bitdinger |
| 5,275,299 A | 1/1994 | Konrad et al. |
| 5,279,576 A | 1/1994 | Loo et al. |
| 5,291,991 A | 3/1994 | Meyer |
| 5,297,599 A | 3/1994 | Bucheli |
| 5,342,319 A | 8/1994 | Watson et al. |
| 5,348,548 A | 9/1994 | Meyer et al. |
| 5,350,372 A | 9/1994 | Ikeda et al. |
| 5,352,196 A | 10/1994 | Haber et al. |
| 5,358,501 A | 10/1994 | Meyer |
| 5,360,413 A | 11/1994 | Leason et al. |
| 5,364,386 A | 11/1994 | Fukuoka et al. |
| 5,385,546 A | 1/1995 | Kriesel et al. |
| 5,397,303 A | 3/1995 | Sancoff et al. |
| 5,409,125 A | 4/1995 | Kimber et al. |
| 5,411,499 A | 5/1995 | Dudar et al. |
| 5,415,374 A | 5/1995 | Carroll et al. |
| 5,419,256 A | 5/1995 | Pollich |
| 5,421,814 A | 6/1995 | Geary |
| 5,423,791 A | 6/1995 | Bartlett |
| 5,425,465 A | 6/1995 | Healy |
| 5,429,256 A | 7/1995 | Kestenbaum |
| 5,433,330 A | 7/1995 | Yatsko et al. |
| 5,433,703 A | 7/1995 | Utterberg et al. |
| 5,435,282 A | 7/1995 | Haber et al. |
| 5,437,648 A | 8/1995 | Graves et al. |
| 5,441,487 A | 8/1995 | Vedder |
| 5,454,409 A | 10/1995 | McAffer et al. |
| 5,454,805 A | 10/1995 | Brony |
| 5,466,219 A | 11/1995 | Lynn et al. |
| 5,470,319 A | 11/1995 | Mayer |
| 5,470,327 A | 11/1995 | Helgren et al. |
| 5,474,541 A | 12/1995 | Ritsky et al. |
| 5,474,544 A | 12/1995 | Lynn |
| 5,487,737 A | 1/1996 | Meyer |
| 5,494,170 A | 2/1996 | Burns |
| 5,501,676 A | 3/1996 | Niedospial et al. |
| 5,514,116 A | 5/1996 | Vaillancourt et al. |
| 5,514,117 A | 5/1996 | Lynn |
| 5,520,641 A | 5/1996 | Behnke et al. |
| 5,520,642 A | 5/1996 | Bigagli et al. |
| 5,520,661 A | 5/1996 | Lal et al. |
| 5,520,665 A | 5/1996 | Fleetwood |
| 5,520,666 A | 5/1996 | Choudhury et al. |
| 5,533,983 A | 7/1996 | Haining |
| 5,533,994 A | 7/1996 | Meyer |
| 5,549,575 A | 8/1996 | Giambattista et al. |
| 5,549,651 A | 8/1996 | Lynn |
| 5,566,729 A | 10/1996 | Grabenkort et al. |
| 5,573,516 A | 11/1996 | Tyner |
| 5,573,520 A | 11/1996 | Schwartz et al. |
| 5,573,525 A | 11/1996 | Watson et al. |
| 5,573,526 A | 11/1996 | Hess |
| 5,576,392 A | 11/1996 | Yamamoto et al. |
| 5,598,939 A | 2/1997 | Watson et al. |
| 5,613,291 A | 3/1997 | Solomon et al. |
| 5,616,129 A | 4/1997 | Mayer |
| 5,616,130 A | 4/1997 | Mayer |
| 5,620,434 A | 4/1997 | Brony |
| 5,641,010 A | 6/1997 | Maier |
| 5,662,230 A | 9/1997 | Finneran |
| 5,685,845 A | 11/1997 | Grimard |
| 5,697,915 A | 12/1997 | Lynn |
| 5,702,019 A | 12/1997 | Grimard |
| 5,709,666 A | 1/1998 | Reynolds |
| 5,718,348 A | 2/1998 | Manera |
| 5,776,124 A | 7/1998 | Wald |
| 5,776,125 A | 7/1998 | Dudar et al. |

| | | | | | | |
|---|---|---|---|---|---|---|
| 5,785,701 A | | 7/1998 | Sams et al. | 5,931,828 A | 8/1999 | Durkee |
| 5,803,284 A | | 9/1998 | Grimard | 5,954,104 A | 9/1999 | Daubert et al. |
| 5,819,964 A | | 10/1998 | Grimard | 5,957,898 A | 9/1999 | Jepson et al. |
| 5,833,089 A | | 11/1998 | Manni et al. | 6,003,566 A | 12/1999 | Thibault et al. |
| 5,855,575 A | | 1/1999 | Solomon et al. | 6,050,435 A | 4/2000 | Bush et al. |
| 5,857,579 A | * | 1/1999 | Finneran ............... 215/252 | 6,056,135 A | 5/2000 | Widman |
| 5,863,655 A | | 1/1999 | Mock | 6,070,623 A | 6/2000 | Aneas |
| 5,873,872 A | | 2/1999 | Thibault et al. | 6,071,270 A | 6/2000 | Fowles et al. |
| 5,879,345 A | | 3/1999 | Aneas | 6,159,192 A | 12/2000 | Fowles et al. |
| 5,891,129 A | | 4/1999 | Daubert et al. | | | |
| 5,925,029 A | | 7/1999 | Jansen et al. | | | |

\* cited by examiner

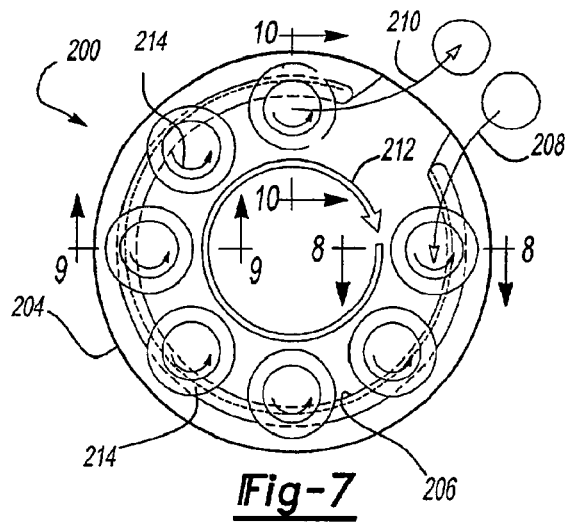
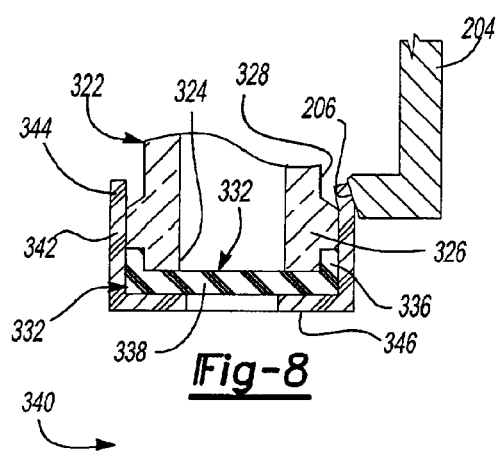
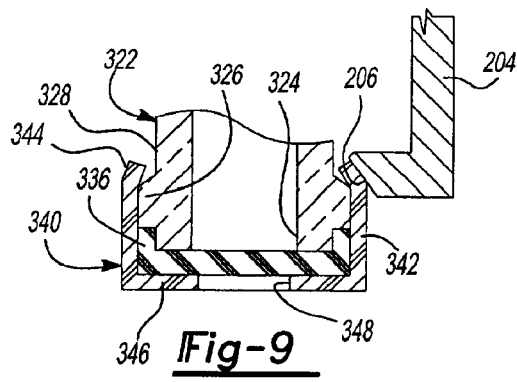
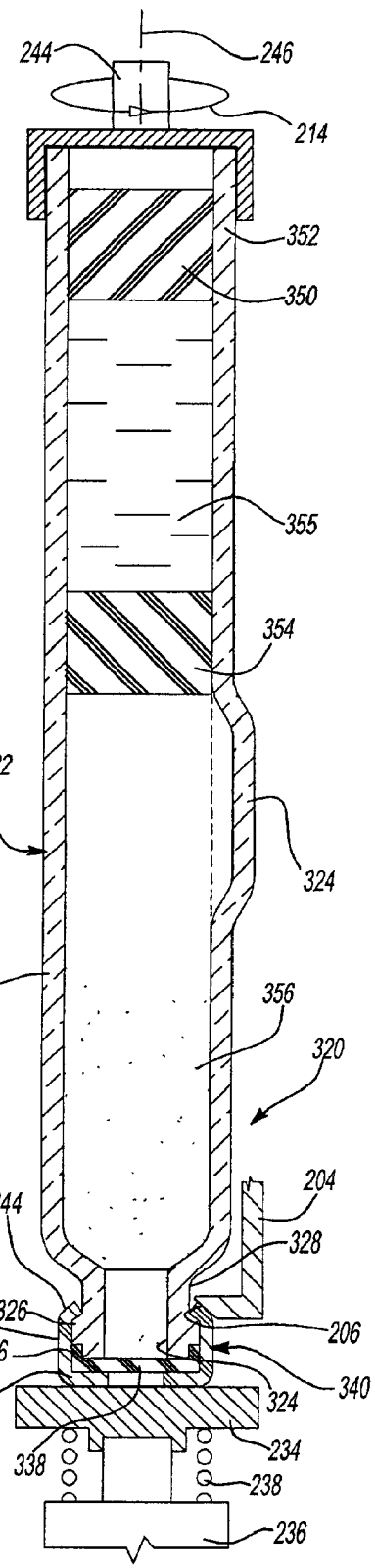

METHOD OF SEALING A CARTRIDGE OR OTHER MEDICAL CONTAINER WITH A PLASTIC CLOSURE

RELATED APPLICATIONS

This application is a continuation in part application of Ser. No. 09/732,538 filed Dec. 8, 2000 now U.S. Pat. No. 6,681,475 and Ser. No. 09/421,657 filed Oct. 20, 1999, abandoned, which applications are continuation-in-part applications of Ser. No. 09/168,502 filed Oct. 8, 1998, now U.S. Pat. No. 6,382,442 which claims priority under 35 U.S.C. Section 119e to U.S. Provisional Application Ser. No. 60/082,372, filed Apr. 20, 1998.

FIELD OF THE INVENTION

This invention relates to an improved method of sealing a medical cartridge or other medical container containing a medicament, drug or vaccine, which eliminates the problems associated with malleable metal caps or collars, such as aluminum. The method of this invention may be used to seal a cartridge having an elastomeric stopper with a polymeric cap or closure.

BACKGROUND OF THE INVENTION

It is conventional to store medicaments, drugs or vaccines in a sealed cartridge or other container for later use. Such medicaments, drugs or vaccines may be in liquid or dry or powdered form to increase the shelf life of the drugs and reduce inventory space. Such dry or powdered medicaments, drugs or vaccines are generally stored in a sealed cartridge and reconstituted in liquid form for administration to a patient by adding a diluent or solvent. A conventional medical cartridge for storing medicaments generally includes an open end, a radial rim portion surrounding the open end and a reduced diameter neck portion adjacent the rim portion. The cartridge is conventionally sealed with an elastomeric stopper or septum which generally includes a central portion overlying the open end of the cartridge and a planar radial rim portion which overlies the cartridge rim. The stopper is normally secured to the cartridge with a thin malleable metal cap, such as aluminum. The aluminum cap includes a tubular portion which surrounds the rim portions of the stopper and cartridge, an inwardly projecting annular portion which overlies the rim portion of the stopper and a distal end portion which is crimped radially into the neck of the cartridge beneath the rim portion. Because aluminum is malleable, the collar accommodates the buildup of tolerances of the dimensions of the stopper and rim. The dimensions and tolerances of standard cartridges and stoppers are set by the International Standards Organization (ISO).

The radial portion of the aluminum cap which overlies the stopper rim portion may be closed, in which case the aluminum cap is removed by "peeling" the aluminum cap from the cartridge. A pre-slit tab located in the middle area may be provided which overlies the cartridge rim, permitting the cap to be torn from the top and peeled from the cartridge prior to use. This closed embodiment of an aluminum cap has several disadvantages. First, the tearing of the metal cap creates sharp edges which may cut or damage sterile gloves and cut the person administering the drug, thereby exposing both the healthcare worker and the patient to disease and contamination of the drug. Second, the tearing of the aluminum cap generates metal particles which may also contaminate the drug, medicament or vaccine. The dangers associated with the tearing of an aluminum cap has been solved in part by adding a "flip-off" plastic cap. In one such embodiment, the aluminum collar includes a central opening and a shallow plastic cup-shaped cap is received over the aluminum collar having a central projecting riveting portion which is received and secured in the central opening of the aluminum collar. The plastic cap is then removed by forcing the flip-off cap away from the aluminum collar, which tears an annular serrated portion surrounding the central opening and exposes an opening in the collar for receipt of a needle cannula or the like. This embodiment reduces but does not eliminate the possibility of tearing the sterile gloves of the healthcare worker. More importantly, however, aluminum dust is still created during crimping of the aluminum cap which may contaminate the medicament, drug or vaccine contained in the cartridge. It is also important to note that metallic dust is also created simply by forming and affixing the aluminum cap or collar to the cartridge because aluminum dust is created in forming the aluminum collar, crimping of the collar and removal.

Various types of medical cartridges are now available for delivery of a medicament, drug or vaccine. A medical cartridge includes a tubular barrel portion, typically formed of glass, having open proximal and distal ends, wherein the proximal end includes a radial rim portion and a reduced diameter neck portion adjacent the rim portion. The proximal open end of the cartridge is sealed with an elastomeric stopper having a central portion overlying the open proximal end of the cartridge and a rim portion overlying the rim portion of the cartridge. The proximal open end of the cartridge is sealed with a malleable metal cap generally formed of aluminum including a tubular collar portion surrounding the rim portion of the cartridge which is crimped around the rim portion into the neck portion of the cartridge. The cap further includes a radial portion overlying the rim portion of the elastomeric stopper and the cap generally includes a central circular opening coaxially aligned with the opening through the proximal end of the cartridge. The cap is secured to the proximal end of the cartridge by resiliently compressing the radial portion of the cap against the rim portion of the elastomeric stopper and crimping the free end of the collar portion into the neck portion of the cartridge.

The open distal end of the cartridge is sealed with a stopper, generally formed of an elastomeric material, which serves as a plunger to propel the fluid through the proximal open end of the cartridge. The cartridge may be utilized in a delivery pen, for example, as disclosed in U.S. Pat. No. 5,549,575 assigned to the assignee of the present application, the disclosure which is incorporated herein by reference. A delivery pen typically includes a needle assembly received on the proximal end of the body portion having a needle cannula which pierces the elastomeric stopper or septum which seals the proximal end of the cartridge and the stopper in the distal end of the cartridge is then driven through the barrel portion to dispense a liquid medicament, drug or vaccine through the needle cannula during an injection. The medical cartridge may also include a third stopper centrally located within the barrel portion which, during injection, intermixes the substances contained in the barrel portion between the stoppers as discussed further below.

The need therefore remains for a method of sealing cartridges and other medical containers which may be utilized for sealing conventional medical cartridges, which assures sealing of the container and which achieves a good level of cleanliness, without metal particles or dust which may contaminate the medicament, drug or vaccine, and which does not expose the health care worker to sharp edges.

The method of sealing a medical container of this invention solves these problems and permits sealing of medical containers in an aseptic environment.

SUMMARY OF THE INVENTION

As set forth above, the method of sealing a cartridge or other medical container with a plastic closure of this invention eliminates the problems associated with malleable metal or aluminum caps or collars, but which accommodates build-up of tolerances of the rim portion of the container and the elastomeric stopper, when used. The plastic or polymeric closure of this invention is relatively inexpensive to manufacture and use in the method of this invention. The method of this invention may be utilized to seal a conventional medical cartridge with a polymeric cap and for transferring fluids between the stoppers of a medical cartridge. As used herein, the term "closure" is generic to either a cap or collar.

As stated above, the method of sealing a container with a plastic closure of this invention may be utilized with a conventional cartridge or other medical container having an open proximal end, a radial rim portion surrounding the proximal open end and a reduced diameter neck portion adjacent the rim portion. The method of sealing a medical cartridge or other container with a plastic closure of this invention includes forming a plastic closure from a polymer, preferably formed by injection molding, which is sufficiently malleable to permit radial deformation, yet sufficiently rigid to retain its shape following deformation and sufficiently resistant to creep to maintain a seal between the plastic closure and the cartridge rim following radial deformation. The plastic closure formed by the method of this invention includes a generally cylindrical tubular collar portion having an internal diameter generally equal to or preferably slightly greater than an outside diameter of the rim portion of the container and an integral radial rim portion preferably having a central opening. In the preferred method of this invention, the plastic closure is formed by injection molding a polymer alloy comprising a relatively malleable soft polymer and a relatively rigid polymer. The closure may be formed by co-injecting a polymer alloy which preferably includes a polycarbonate as the relatively rigid polymer.

The method of this invention then includes telescopically disposing the tubular portion of the closure over the rim portion of the container with the radial rim portion of the closure overlying the rim portion of the container and the generally cylindrical tubular portion surrounding the container rim having a free end surrounding the reduced diameter neck portion of the container. The tubular portion of the closure adjacent the free end is then incrementally deformed and rolled radially inwardly into the neck portion of the container beneath the rim portion and preferably against the rim portion adjacent the neck portion, permanently securing the closure on the container and sealing the container open end, wherein the free end of the plastic closure retains its shape beneath the radial rim portion following deformation and the polymer is sufficiently resistant to creep to permanently maintain the seal. In the preferred method of sealing a cartridge having medicament, drug or vaccine therein, the cartridge is initially sealed with an elastomeric stopper having a planar rim portion which overlies the rim portion of the cartridge. The method of this invention then preferably includes compressing the radial rim portion of the plastic closure against the radial portion of the stopper to seal the plastic closure to the stopper and substantially simultaneously radially incrementally deforming and rolling the free end of the closure tubular portion into the reduced diameter neck portion of the cartridge as described above.

In the preferred method of sealing a container, such as a medical cartridge, with a plastic or polymeric closure of this invention, the cylindrical tubular portion of the closure is incrementally deformed radially and rolled into the neck portion of the container using a crimping tool or tools having inclined, chamfered or tapered surfaces and the cartridge or container and the crimping tool are relatively rotated and driven together to deform or incrementally roll the tubular portion of the closure both radially into the neck portion of the collar and axially against the adjacent rim portion of the container to permanently secure the closure on the container and seal the container. In one preferred embodiment of the method of this invention, the crimping tool includes a plurality of frustoconical chamfered surfaces which are rotated and driven against the tubular portion of the closure, incrementally rolling the collar into the neck portion of the cartridge as described. In this embodiment, the cartridge or container may be simultaneously rotated to incrementally crimp and seal the entire periphery of the rim portion. In another embodiment, the crimping tool includes an arcuate or circular stationary rail having an inclined or frustoconical chamfered surface and the method of crimping the closure includes simultaneously driving the cartridge and closure assembly against the rail and rotating the cartridge assembly to incrementally roll the free end of the tubular portion of the closure radially inwardly into the reduced diameter neck portion and axially against the adjacent rim portion of the cartridge as described. In either embodiment, the method is preferably a cold forming process dependent upon the material of the polymeric closure, which as described as above is sufficiently malleable to permit radial deformation, yet sufficiently rigid to retain its shape following deformation and sufficiently resistant to creep to maintain the seal between the plastic closure and the cartridge following radial deformation.

In both preferred embodiments of cold forming by incrementally rolling the free end of the plastic closure into the reduced diameter neck portion of the cartridge or other container, the free end of the tubular collar portion is preferably gradually or incrementally deformed radially into the neck portion to assure permanent deformation, reduced creep and reduce damage to the closure, such as stress cracking or discoloration of a clear plastic closure. In the first embodiment of the method of this invention described above, the free end of the tubular closure is deformed incrementally by a series of rotating crimping tools, wherein the first tool has a relatively steep angle of inclination, such as 45 degrees. The angle of inclination of the next crimping tool is then reduced, etc. to the desired angle of the deformed lip, which may be, for example, 20 to 30 degrees. In the second embodiment of the method of this invention described above, the angle of inclination of the crimping surface of the rail is gradually and continuously reduced as the cartridge or other container is rolled or rotated along the rail gradually cold forming and rolling the free end of the closure into the cartridge neck thereby avoiding damage to the cartridge rim portion and the closure, including cracking and discoloration.

One important advantage of the method of sealing a cartridge or other medical container of this invention is that the container may be a conventional medical cartridge, as described above, having a conventional elastomeric stopper.

The method of sealing a transfer set on a cartridge or other medical container with a plastic closure of this invention then includes first assembling the stopper or stoppers on the medical cartridge. The closure is then assembled on the cartridge or other medical container by telescopically receiving the tubular collar portion of the closure over the rim portion of the cartridge such that the tubular collar portion surrounds the rim portion of the cartridge and at least a portion of the reduced diameter neck portion. The method of this invention then includes incrementally rolling and radially deforming the free end of the tubular collar portion of the closure into the reduced diameter neck portion of the container and preferably against the adjacent radial rim portion, permanently securing the closure on the cartridge and sealing the cartridge as described above. That is, the tubular collar portion is preferably gradually or incrementally deformed or cold rolled as described above. In the most preferred embodiment of the method of sealing a cartridge of this invention, the radial portion of the closure is simultaneously compressed against the radial planar rim portion of the elastomeric stopper on the proximal open end of the cartridge as the tubular collar portion is incrementally crimped into the neck portion of the cartridge As set forth above, the method of sealing a cartridge or other medical container with a plastic closure of this invention utilizes a polymer for the closure having the requisite physical properties to provide and maintain a seal between the plastic closure and the cartridge or other medical container and permanently secure the closure on the container. In the preferred embodiment, the plastic closure is formed of a polymer alloy or melt blend which includes a relatively tough soft malleable copolymer and a relatively rigid copolymer. In the most preferred embodiment, the composite polymer is a polymeric alloy of a relatively soft malleable copolymer and a relatively rigid polymer. The preferred rigid polymer is a polyamid or a polycarbonate and the preferred relatively soft copolymer may be selected from polyesters or polyolefins. The resultant polymer alloy or composite preferably has an elongation at yield between 5% and 10% and an elongation at break greater than 100% with a flectural modulus of greater than 1,900 MPa.

The method of this invention thus eliminates the problems and hazards associated with the use of a malleable metal closure or collar, such as aluminum, and plastic coated aluminum caps or collars while assuring sealing of the cartridge or other medical container or damage to the plastic closure or cartridge rim portion. In the most preferred embodiment of the method of this invention, the plastic closure or collar is formed by injection molding the plastic closure from a polymeric alloy or composite as described. A thermoplastic elastomer may also be co-injected with the polymer forming the closure to form a coating or film on the inside surface of the closure, which is integrally bonded to the polymer of the closure. As used herein, the terms "composite" and "alloy" are used in their broadest sense to include alloys or melt blends, composites and copolymers.

Other advantages and meritorious features of the method of sealing a cartridge or other medical container with a plastic closure or collar of this invention will be more fully understood from the following description of the preferred embodiments, the appended claims and the drawings, a brief description of which follows.

BRIEF DESCRIPTION OF THE DRAWINGS

FIGS. 4 to 6 illustrate one preferred method of crimping a closure on the medical cartridge shown in FIGS. 1 and 3, wherein FIG. 4 is a perspective top view;

FIG. 5 is a partially cross-sectioned side view of FIG. 4 in the direction of view arrows 5—5; and FIG. 6 is an enlarged side partially cross-sectioned view of FIG. 4 in the direction of view arrows 6—6;

FIGS. 7 to 10 illustrate an alternative method of sealing a cartridge, wherein FIG. 7 is a top perspective view and FIGS. 8 to 10 are a side partially cross sectioned views in the direction of view arrows 8—8, 9—9 and 10—10, respectively;

DETAILED DESCRIPTION OF THE PREFERRED EMBODIMENTS

Figure 1:
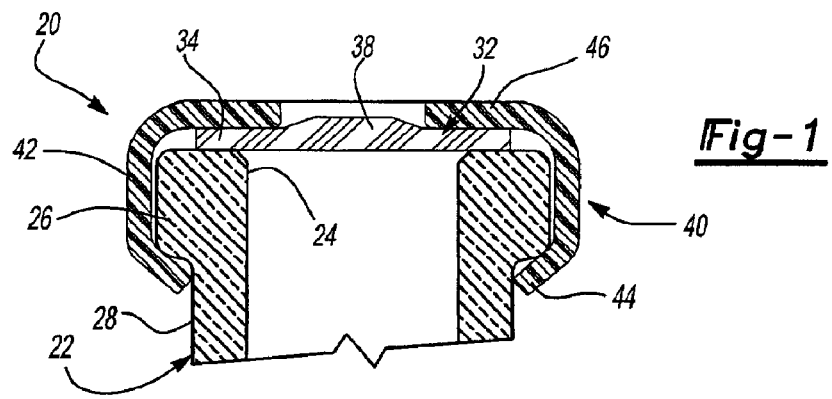
FIG. 1 is a partial side cross-sectional side view of a plastic closure secured to a medical cartridge in sealed relation formed by the method of this invention.
Figure 2:
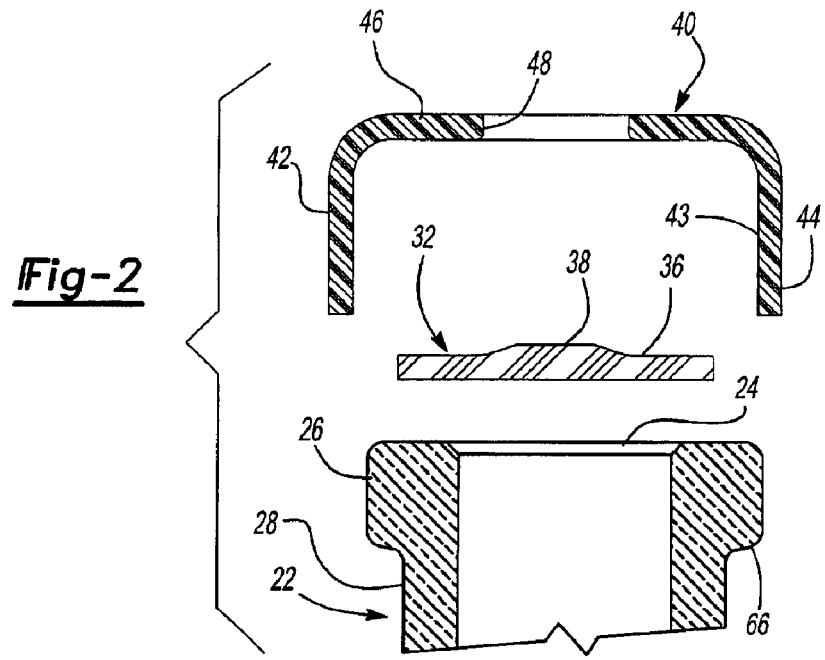
FIG. 2 is an exploded side cross-sectional view of the components of the assembly shown in FIG. 1 illustrating the method of assembling the closure and stopper on the cartridge.
Figure 3:
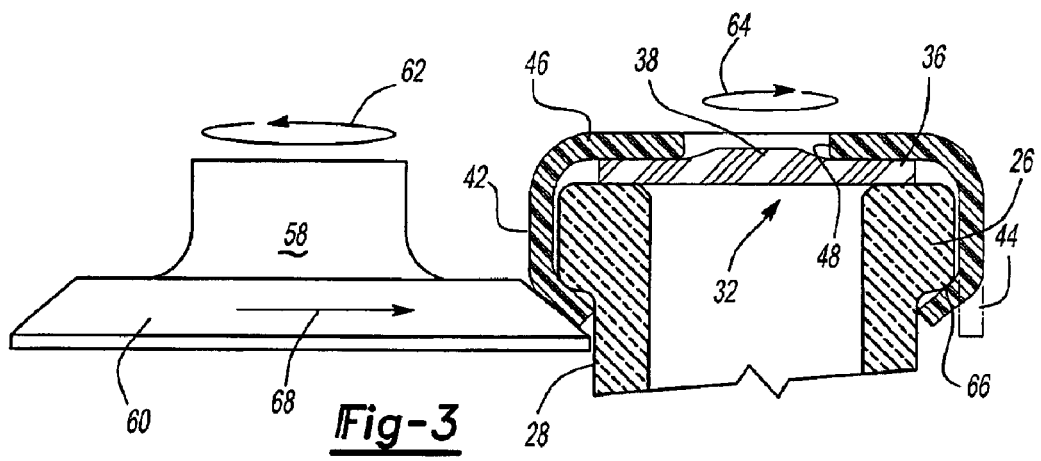
FIG. 3 is a partially cross-sectioned side view of the assembly shown in FIGS. 1 and 2 schematically illustrating one embodiment of the method of crimping the closure on the cartridge.

FIGS. 1 to 3 illustrate one preferred embodiment of the cartridge, stopper and closure assembly 20 sealed by the method of this invention. As set forth above, the method of this invention may be utilized to seal various containers and is particularly useful for sealing the proximal end of a medical cartridge 22 illustrated in FIGS. 1 to 3. The cartridge includes an open proximal end 24, an annular radially extending rim portion 26 and a reduced diameter neck portion 28 adjacent the rim portion. As shown, the neck portion 28 of the cartridge has a reduced diameter when compared to the rim portion 26 and the container portion 30 shown in FIG. 6. Medical cartridges of this type are generally formed of glass but may also be formed of a sterilizable plastic. The open end 24 of the cartridge is typically closed with an elastomeric stopper 32 having a planar rim portion 36 which overlies the rim portion 26 of the cartridge as shown in FIG. 1. The stopper is generally formed of a resilient elastomeric material such as synthetic or natural rubber. The central portion 38 of the stopper may be pierced with a hypodermic needle, for example, to either withdraw fluid from the cartridge or add a solvent or diluent to the cartridge where the medicament, drug or vaccine in the cartridge is a dry or powdered material.

A preferred embodiment of the closure or cap 40 is shown in FIG. 1 attached to a cartridge 22 and stopper 32 assembly, prior to assembly in FIG. 2 and during assembly in FIG. 3. This embodiment of the closure 40 includes a tubular collar portion 42 which surrounds the rim portion 26 of the cartridge and the planar rim portion 36 of the stopper. Where the external surface of the rim portion 26 of the cartridge is cylindrical, the tubular collar portion 42 of the closure will generally also be cylindrical. As shown in FIG. 1 and described below, the free end 44 of the tubular collar portion 42 is incrementally deformed radially inwardly and rolled into the reduced diameter neck portion 28 and against the adjacent surface of the rim portion 26 of the cartridge, permanently securing the collar 40 on the cartridge and sealing the cartridge and avoiding damage to the polymeric closure and rim portion of the cartridge. The preferred embodiment of the closure 40 also includes an integral radial proximal portion 46 which overlies the rim portions 26 and 36 of the cartridge and stopper, respectively. The radial portion 46 is preferably integrally molded with the tubular collar portion 42 of the closure. This embodiment of the closure 40 also includes a central opening 48 which overlies the central portion 38 of the stopper, preferably coaxially aligned with the central portion 38 of the stopper. The central opening 48 may however, be eliminated in certain applications of this invention where the polymeric closure is pierceable. As used herein, the terms proximal and distal are used solely for ease of description, wherein the term proximal refers to elements or portions of elements closest to the rim portion 36 of the stopper and distal refers to elements or portions of elements more remote from the rim portion of the cartridge. Further, the terms cap and collar are sometimes used herein interchangeably.

Figure 6:
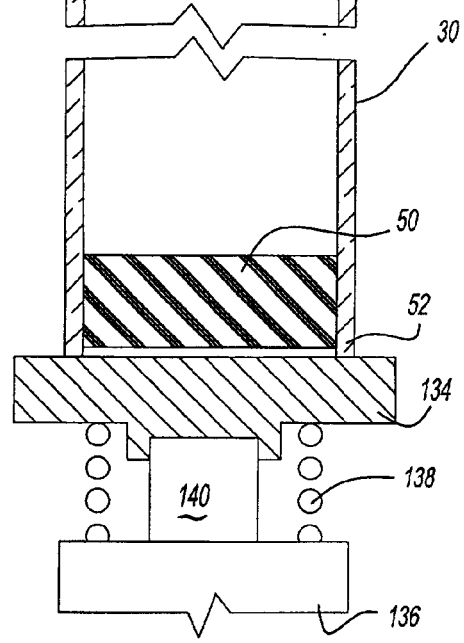

The closure 40 is then assembled on the cartridge 22 and stopper 32 as shown in FIG. 2. In a typical application, a second stopper 50 is first inserted into the distal end 52 of the cartridge 22, after the cartridge is filled as shown in FIG. 6. As set forth above, the plastic closure 40 of this invention may be used with various containers particularly including conventional medical cartridges as shown. Thus, in a typical application, the cartridge 22 may be filled with a medicament, vaccine or drug prior to or after securing the closure 40 on the proximal end of the cartridge. The tubular portion 42 of the closure 40 is then received over the rim portion 36 of the stopper and the rim portion 26 of the cartridge as shown in FIG. 3 and describe below.

A method of crimping the closure or cap 40 on the cartridge 22 is schematically shown in FIG. 3. The free end 44 of the tubular collar portion 42 of the closure is crimped or rolled on the cartridge by a crimping tool 58 having an inclined or tapered surface 60 which, in the disclosed embodiment, is frustoconical. The crimping tool 58 is rotated in one direction as shown by arrow 62 and, in this embodiment, the assembly of the closure 40 and cartridge 22 is rotated at the same speed in the opposite direction as shown by arrow 64 and thereby rolled into the neck 28 of the cartridge. The inclined frustoconical surface 60 is driven against the tubular portion 42 of the closure as shown by arrow 68 or vice versa, which deforms the free end 44 radially inwardly against the reduced diameter neck portion 28 and against the rounded edge 66 of the rim portion 26 adjacent the neck portion 28. The radial portion 46 of the closure is preferably simultaneously compressed against the planar radial rim portion 36 of the elastomeric stopper 32 to assure complete sealing of the cartridge. In the preferred method of sealing a medical container with a closure of this invention, the tubular portion 42 is incrementally deformed and rolled into the reduced diameter neck portion 28 by cold forming. That is, the crimping tool 58 is not heated to soften or partially melt the polymeric closure as would be required with certain polymers. Thus, as described below, the preferred polymer for the closure is selected based upon its physical properties, as described above. In the most preferred embodiment of the method of sealing a cartridge or medical container with a closure of this invention, the tubular portion 42 of the closure is gradually or incrementally deformed and rolled into the reduced diameter neck portion 28 of the cartridge using a plurality of crimping tools having different degrees of inclination or pitch or the rim portion is deformed against a crimping tool having a gradual change of pitch as described below with regard to FIGS. 4 to 6 and 7 to 10 respectively.

The cartridge 22 is now ready for use. As will be understood by those skilled in this art, the cartridge may be filled with a medicament, drug or vaccine and used with a variety of delivery devices, such as the medicament delivery pen disclosed in the above referenced U.S. Pat. No. 5,549,575. The stopper 50 is conventionally received in the distal end 52 of the cartridge 22, which is generally referred to as the barrel of the cartridge. A cartridge of this type may be utilized to deliver liquid medicaments, drugs or vaccines or used to reconstitute a dry or lyophilized medicament, drug or vaccine powder as discussed further in regard to FIGS. 10 and 11, below. The stopper 50 adjacent the distal end 52 of the cartridge serves as a plunger, which is driven through the cartridge barrel. A needle cannula (not shown) pierces the central portion 38 of the stopper 32 to deliver the medicament, drug or vaccine through the needle cannula as is well known in this art.

The polymer selected for the plastic cap or closure 40 and method of this invention can best be described by its required physical properties. The polymer must be sufficiently malleable to permit radial deformation or crimping, yet sufficiently rigid to retain its shape following deformation. The polymer must also be sufficiently resistant to creep to maintain the seal between the plastic collar portion and the container following radial deformation. It has been found that a polymer having an elongation at yield between 5% and 10% and an elongation at break greater than 100%, combined with a flexural modulus of greater than 1900 MPa has superior performance. Where the plastic closure of this invention is utilized for sealing cartridges containing a medicament, vaccine or drug, the polymer should also be sterilizable and, in certain applications such as the plastic closure for a cartridge transfer set described below, the polymer is preferably relatively clear and maintains its clarity under the stress of deformation or crimping. It has been found that certain polymer alloys or composite polymers including melt blends or alloys and co-polymers having polymers of different malleability and rigidity are preferred in these applications. That is, the plastic closure used in the method of this invention is preferably formed of a polymer alloy, composite polymer or co-polymer including a relatively rigid polymer and a tough relatively soft malleable co-polymer. The most preferred polymer is a polymer alloy or melt blend including a polyamid or polycarbonate as the rigid polymer providing the strength and resistance to creep desired for this application. The relatively soft malleable co-polymer may be selected from various polymers including polyesters and polyolefins; however, a polymer alloy including a polycarbonate or polyamid and a polyester has been found particularly suitable for this application.

As will be understood, various polymeric melt blends, alloys, composites and copolymers are being developed on a rapidly increasing basis and therefore the plastic collar of this invention is not limited to a specific polymer, provided the polymer has the desired physical properties described above. Suitable polymers for the plastic closures of this invention include EASTAR® MB polymers, which are melt blend and alloy polymers and EASTAR® thermoplastic polymers, which are neat polymers sold by Eastman Chemical Company of Kingsport, Tennessee and Eastman Chemical AG of Zug, Switzerland under the trade names "DA003, DN003" and "DN004". These materials are polymeric melt blends, alloys and copolymers of polycarbonate or polyamid and polyester. As used herein, the terms melt blends and alloys refer to polymeric compositions having two or more polymers of different physical properties or characteristics, such as the EASTAR® polymers of Eastman Chemical Company described above which include a polycarbonate or polyamid and a polyester. The polymer selected for the plastic collar of this invention may also include fillers and other constituents which would be more accurately described as a composite, although the base polymers may still be a polymeric melt blend or alloy. As used herein, the term alloy is used in its broadest sense to include alloys or melt blends, composites and co-polymers. As will be understood, the manufacturer or supplier of the raw material will normally blend the polymers based upon the specifications of the customer. The polymers may be co-injected to form a polymeric melt blend, alloy or composite or formed by any other suitable processes. It is anticipated, however, that other polymers having the described physical characteristics may also be utilized in the plastic collar or cap of this invention. In certain applications, it may also be desirable to coat at least the interior surface 43 of the collar shown in FIG. 2 with a thermoplastic elastomer, or the entire collar may have a thin layer of a thermoplastic elastomer. The thermoplastic elastomer coating may be applied as a film or by co-injection with the polymer forming the collar 40. The closure 40 may be formed by injection molding.

FIGS. 4 to 6 and FIGS. 7 to 10 illustrate preferred alternative methods of crimping the closure or cap on a conventional cartridge, wherein the collar or cap 40 is gradually or incrementally deformed and rolled into the neck portion of the cartridge by cold forming. The embodiment of the crimping apparatus and method illustrated in FIGS. 4 to 6 may be utilized to seal cartridges or other containers with a plastic or elastomeric closure up to about 200 cartridges per minute. The crimping apparatus and method disclosed in FIGS. 7 to 10 may be used for higher volume applications, wherein the through put may be as great as 600 cartridges per minute.

Figure 4:
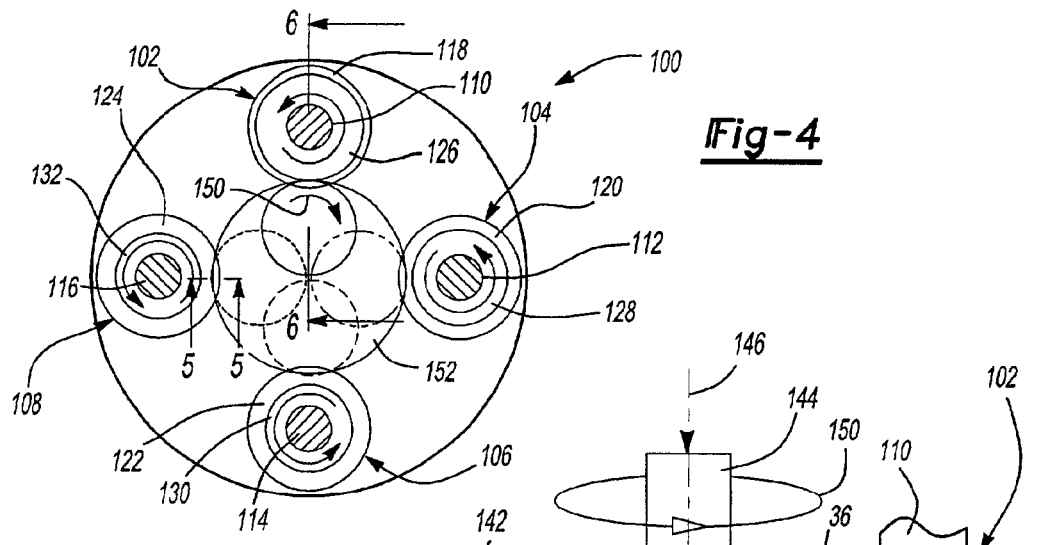
Figure 5:
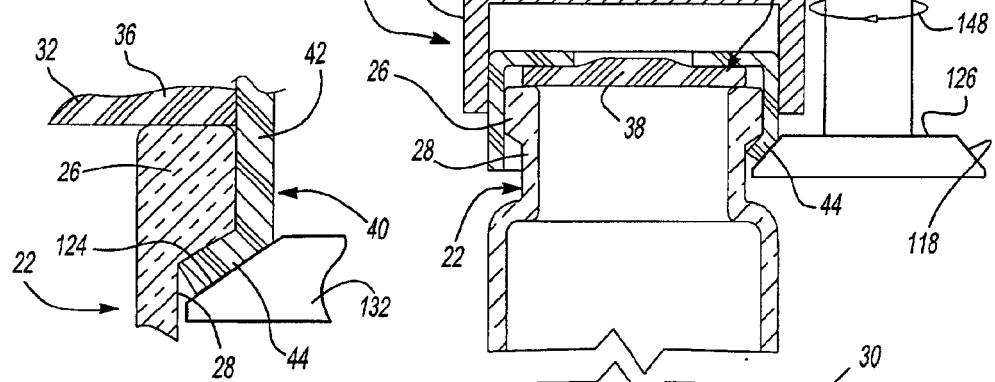

In the embodiment of the crimping or capping apparatus disclosed in FIGS. 4 to 6, the crimping apparatus 100 includes a plurality of crimping tools, wherein the inclined surfaces of the crimping tools each have differing degrees of pitch, incrementally deforming and rolling the free end 44 of the tubular portion 42 of the cap as now described. The embodiment of the crimping apparatus 100 shown in FIG. 4 includes four rotatable crimping tools 102 to 108, each having a shaft 110 to 116, respectively, and an inclined or tapered surface 118 to 124, respectively, on the roller portion of the crimping tools 126 to 132, respectively. The pitch or angle of inclination of the inclined surfaces 118 to 124 decreases progressively as the cartridge progresses through the stations of the crimping apparatus. That is, the pitch of the inclined surface 120 of crimping tool 104 of the second station is less than the pitch of the inclined surface 118 of the crimping tool 102 of the first station, etc.

FIG. 6 illustrates the first station of the crimping apparatus 100. The cartridge, stopper closure assembly 20 is supported on a support member 134, which is preferably resiliently biased to compress the radial portion 46 against the rim portion 36 of the elastomeric stopper 32 during crimping as set forth above. In the disclosed embodiment, the cartridge 22 is supported on a support member 134, which is supported on a base 136 by piston 140 and is spring biased by a suitable resilient member, such as spring 138. The upper or proximal end of the cartridge 22 and cap 40 is supported by a cup-shaped support member 142 which is affixed to rotatable shaft 144. The cup-shaped support member 142 may also be spring biased downwardly as shown by arrow 146. The assembly 20 is then rotated against the rotatable crimping tool 102 in the first station, which includes a rotatable shaft 110 having a roller portion 126. As set forth above, the roller portion 126 includes an inclined or tapered surface 118 which incrementally deforms the free end 44 of the tubular collar portion 42 radially inwardly into the reduced diameter neck portion 28 of the cartridge 22. The relative rotation of the crimping tool 102 and the cartridge assembly is shown by arrows 148 and 150, wherein the crimping tool and cartridge assembly are rotated at the same speed in opposite directions. As will be understood, however, one of the crimping tool and cartridge assembly may be the drive member and the other may be the driven member wherein only the drive member is rotated and the other member follows. The base 136 is supported in the disclosed embodiment on a turntable 152, as shown in FIG. 4, such that the cartridge assembly is moved from station to station. In the first station, as shown in FIG. 6, the inclined surface 118 has a relatively steep angle, which deforms the free end 44 only partially into the reduced diameter neck portion 28 as shown at the right side of FIG. 6. As set forth above, the inclined surface of the crimping tool at each station is reduced, such that the crimping tool in the final station 108 deforms the free end 44 of the tubular collar portion 42 into and against the reduced diameter neck portion and against the adjacent surface of the rim portion 26 of the cartridge barrel as shown in FIG. 5. The crimping apparatus 100 thus performs the method of this invention as described above. That is, the free end 44 of the cap or closure 40 is incrementally deformed and rolled into the neck portion 28 by the plurality of crimping tools avoiding stress cracking and discoloration of the clear polymeric cap.

FIGS. 7 to 10 illustrate a preferred alternative crimping apparatus 200, wherein the crimping tool includes a circular rail 202 supported on a suitable support 204. The rail 202 includes an inclined surface 206 which gradually and continuously changes in pitch from the inlet 208 to the outlet 210. That is, the tubular collar portion 204 is driven against the tapered surface 206 at the inlet 208 and the pitch of the tapered surface is continuously decreased along the rail to the outlet 210. The cartridge assembly 320 illustrated in FIGS. 7 to 10 and best shown in FIG. 10 includes a cartridge or cartridge barrel 322 having an open end 324, a radial rim portion 326 adjacent to but spaced from the open end 324 and a reduced diameter neck portion 328. The container portion 330 in this embodiment includes an enlarged bypass portion 324, the purpose of which is described below. The proximal open end 324 of the cartridge includes a cup-shaped stopper 332 including a tubular rim portion 336 and a central portion 338. As shown in FIGS. 7 to 10, the rim portion 336 of the cup-shaped stopper engages the rim portion 326 of the cartridge barrel. The closure of cap 340 is similar to the cap 40 described above in regard to FIGS. 1 to 3, except that the tubular portion 342 is essentially perpendicular to the radial portion 346 to accommodate the cup-shaped stopper 332. The closure 340 includes a central opening 348 and the tubular collar portion 342 includes a free end 344 surrounding the reduced diameter neck portion 328 as best shown in FIGS. 8 to 10.

The distal open end 352 of the cartridge barrel includes a second stopper 350 as described above. In this embodiment, however, the cartridge assembly includes a third stopper 354 spaced from the second stopper 350 adjacent the bypass 324. Thus, the cartridge assembly 320 best shown in FIG. 10 may include a combination of medicaments, drugs or vaccines or a liquid 355, such as a diluent and a dry or powdered medicament, drug or vaccine 356. Thus, as the second stopper 350 is driven through the cartridge barrel 322 against the liquid 355, the third stopper 354 is driven into the enlarged bypass 324 and the liquid 355 flows around the stopper 354 through the bypass 324 into the powder 356. Where the liquid 355 is a diluent and the substance 356 is a dry or lyophilized medicament, drug or vaccine, the diluent 355 will flow through the bypass 324 and reconstitute the dry or powdered drug, vaccine or medicament 356.

With the crimping apparatus 200 illustrated in FIGS. 7 to 10, the cartridge assembly 320 is continuously rotated as the tubular collar portion is driven against the rail as shown by arrows 212 and 214. FIG. 8, which is a partial cross sectional view through view arrows 8—8, illustrates the initial deformation of the free end 344 tubular collar portion 342 adjacent the entrance 208, wherein the angle of inclination of the chamfered or frustoconical surface 206 is relatively steep, such as about 40 to 50 degrees or greater. FIG. 9, which is a partial cross sectional view through view arrows 9—9, illustrates the angle of inclination of the chamfered surface 206 of the rail 204 about midway through the cold deformation and rolling of the tubular collar portion, wherein the angle of inclination is less than 40 degrees. Finally, FIG. 10 illustrates the angle of inclination 206 of the chamfered surface adjacent the outlet 210, wherein the angle of inclination is less than 30 degrees, fully deforming the free end 344 of the tubular collar portion 342 into the reduced diameter neck portion 328 of the cartridge and against the rim portion 326. Thus, the rim portion is gradually or incrementally deformed and rolled by the continuously decreasing angle of inclination of the chamfered or frustoconical surface 206 in a gradual and continuous process. FIG. 10 also illustrates the simultaneous compression of the radial portion 346 of the collar against the rim portion 336 of the stopper during cold forming of the tubular collar portion 344 as described above in regard to FIG. 6, which is a preferred embodiment of the method of this invention.

Thus, in both of the preferred embodiments of the disclosed apparatus for cold forming the free end of the plastic closure into the reduced diameter neck portion of the cartridge or other medical container as described above and shown in FIGS. 4 to 6 and FIGS. 7 to 10, respectively, the free end is gradually or incrementally deformed radially and rolled into the neck portion to assure permanent deformation, reduce creep which could result in leakage and reduce damage to the closure, such as cracking or discoloration of a clear plastic closure. Thus, the method of this invention provides a simple and relatively inexpensive method of crimping or cold forming a plastic closure or collar which avoids the disadvantages of a malleable metal closure or collar and which assures complete sealing of the cartridge without damage to the polymeric closure and rim portion of the cartridge. The tubular collar portion of the closure or collar may also be deformed into the reduced diameter neck portion of the cartridge or other container by a crimping device (not shown) having a jaw which deforms the free end portion of the tubular collar portion into the neck portion one at a time provided the deformation is gradual to avoid damage to the collar portion.

Figure 11:
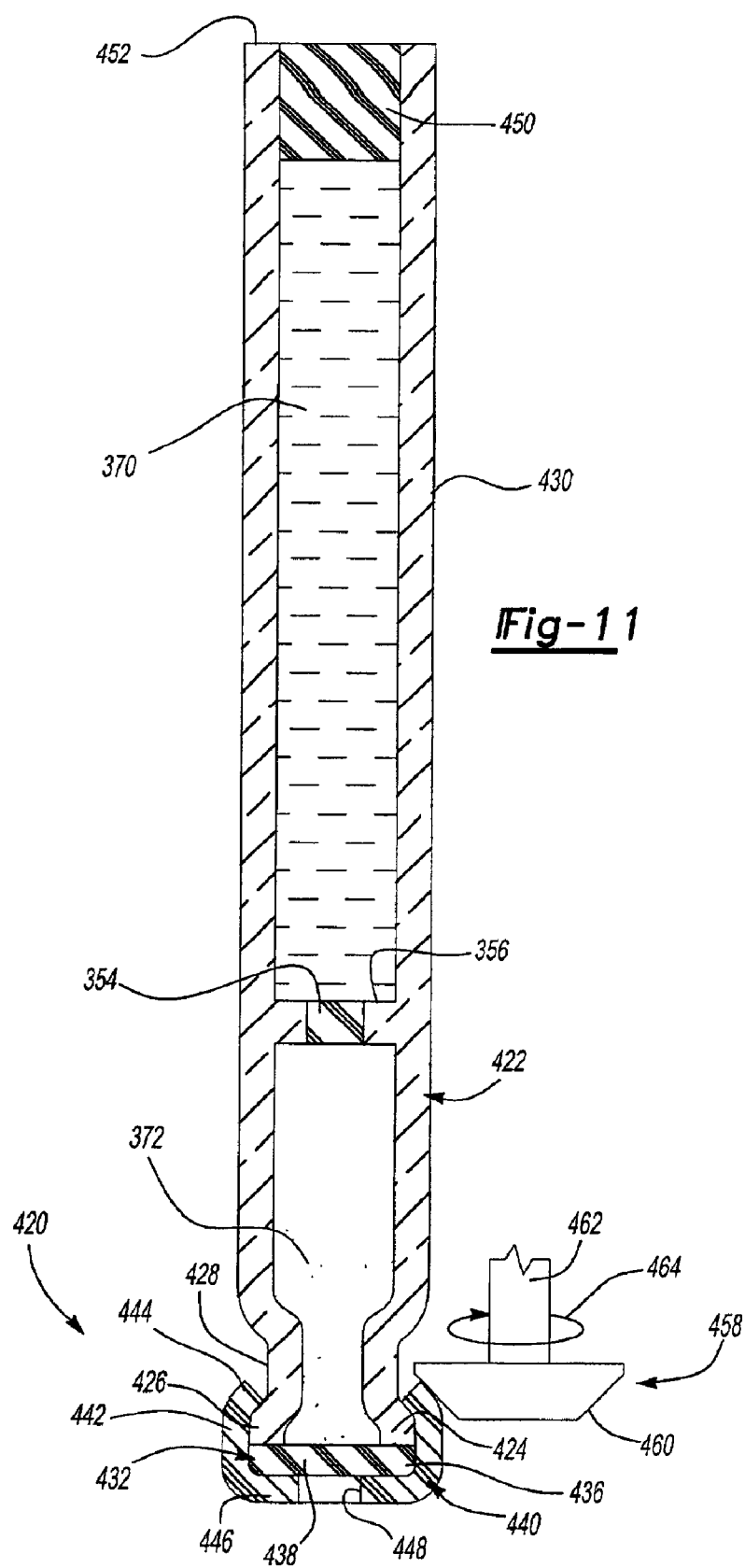
FIG. 11 is a side cross-sectioned view of an alternative embodiment of a cartridge sealed by the method of this invention.

FIG. 11 illustrates an alternative embodiment of a cartridge assembly 420 sealed with a polymeric cap or closure by the method of this invention. The cartridge or cartridge barrel 422 may be formed of glass as described above and includes an open proximal end 424, a radial rim portion 426 surrounding the open end, a reduced diameter neck portion 428 adjacent the neck portion and a container portion 422. An elastomeric stopper 432 is received over the open end having a rim portion 436 received on the rim portion 426 of the cartridge barrel and a center portion 438 bridging the open end. The cap or closure 440 includes a tubular collar portion 422 having a free end 444 which is incrementally deformed and rolled into the reduced diameter neck portion 428 by the method of this invention as described and the cap or closure 440 further includes an integral radial portion 446 received over the rim portion 436 of the stopper and the rim portion 426 of the cartridge barrel. The stopper includes a central opening 448 to receive a needle cannula (not shown) for dispensing the medicament, drug or vaccine contained in the container portion 430 as described below.

In this embodiment of the cartridge assembly 420, the cartridge includes a second stopper 450 received in the open distal end 452 as described above and a third stopper 354 received in an integral radial bridging portion 356 separating the container portion 430 into two compartments 370 and 372 separated by the third stopper 354. The radial deformation of the free end 444 of the cap or stopper 440 is schematically illustrated in FIG. 11 similar to FIG. 3. That is, the free end 444 of the closure 440 is incrementally deformed and rolled into the reduced diameter neck portion 428 of the cartridge barrel 422 by a crimping tool shown schematically at 458 having an inclined surface 460. The crimping tool is rotated on a shaft 462 as shown by an arrow 464. As will be understood, however, from the description of the preferred crimping apparatus disclosed in FIGS. 4 to 6 and 7 to 10 above, the free end 444 of the tubular collar portion 442 is incrementally crimped and rolled into the reduced diameter neck portion 428 of the cartridge barrel either by a plurality of crimping tools having decreasing angles of inclination as disclosed in FIGS. 4 to 6 or a continuous rail having a continuously decreasing angle of inclination as disclosed in FIGS. 7 to 10 thereby avoiding stress cracking or discoloration of the clear polymeric cap or closure 440. The operation of the cartridge assembly 420 shown in FIG. 11 is similar to the cartridge assembly 320 shown in FIG. 10, wherein the second stopper 450 is driven into the first container portion 370 against the liquid contained in this compartment, which drives the third stopper 354 through the opening in the bridge portion 356, intermixing the substances in these compartments which is then dispensed by a needle cannula (not shown) which pierces the central portion 438 of the stopper 432 in a medicament delivery pen such as disclosed in the above referenced U.S. Pat. No. 5,549,575.

The deformation of the free end of the collar portion in each of these embodiments is a cold forming process which, as set forth above, also relies upon the polymer selected for the collar or closure. That is, the polymer selected must be sufficiently malleable to permit radial deformation or crimping without forming stress cracking or fractures. Further, the polymer must be sufficiently rigid to retain its shape following deformation. Finally, the polymer must also be sufficiently resistant to creep to maintain the seal between the plastic closure or collar and the container following radial deformation to prevent leakage or contamination of the materials stored in the container. One important advantage of the method of this invention is that the crimping process may be performed in an aseptic environment preventing contamination of the material within the cartridge and the assembly. As set forth above, another important advantage of the method of this invention is that the improved polymeric closure eliminates the potential contamination and hazards associated with malleable metal closures, such as aluminum. As will be understood, various modifications to the disclosed methods of sealing a cartridge or other container with a polymeric closure of this invention within the purview of the appended claims.

What is claimed is:

1. A method of sealing a medical cartridge with a plastic closure, said medical cartridge including a tubular barrel portion having an open proximal end, a radial rim portion surrounding said open end, a reduced diameter neck portion adjacent said radial rim portion and a resilient stopper overlying said open proximal end and said rim portion of said medical cartridge, said method comprising:

forming a clear plastic closure of a polymer alloy comprising a relatively malleable soft polymer and a relatively rigid polymer, said plastic closure being sufficiently malleable to permit radial deformation, yet sufficiently rigid to retain its shape following deformation, and sufficiently resistant to creep to maintain a seal between the cartridge and the plastic closure following radial deformation, said plastic closure including a generally cylindrical tubular collar portion having an internal diameter generally equal to or slightly greater than an outside diameter of said rim portion of said medical cartridge and an integral radial rim portion;

telescopically disposing said generally cylindrical tubular collar portion of said plastic closure over said rim portion of said cartridge with said radial rim portion of said plastic closure overlying said rim portion of said cartridge and said generally cylindrical tubular collar portion surrounding said rim portion of said cartridge having a free end surrounding said reduced diameter neck portion of said cartridge;

radially deforming said free end of said generally cylindrical tubular collar portion of said plastic closure by incrementally deforming and rolling said free end of said generally cylindrical tubular collar portion into said reduced diameter neck portion of said cartridge beneath said rim portion, said free end of said plastic closure retaining its shape beneath said radial rim portion of said cartridge following deformation to permanently retain said plastic closure on said cartridge and sealing said cartridge proximal open end; and wherein said step of incrementally deforming and rolling said free end of said tubular portion comprises using a crimping tool having an inclined surface, said method including relatively rotating said crimping tool and said medical cartridge with said plastic closure assembled thereon, simultaneously driving said inclined surface against said tubular portion of said closure adjacent said free end, simultaneously cold forming said free end incrementally into said reduced diameter neck portion and against said rim portion of said medical cartridge, permanently deforming said free end into said reduced diameter neck portion and against said rim portion of said medical container.

2. The method of sealing a medical cartridge with a plastic closure as defined in claim 1, wherein said method includes compressing said integral radial rim portion of said plastic closure against said radial portion of said elastomeric stopper to seal said open proximal end and substantially simultaneously incrementally radially deforming and rolling said free end of said closure tubular collar portion into said reduced diameter neck portion of said medical cartridge without discoloration of said clear plastic closure.

3. The method of sealing a medical cartridge with a plastic closure as defined in claim 1, wherein said inclined surface of said crimping tool is frustoconical and said method includes rotating said medical cartridge with said plastic closure assembled thereon and rotating said crimping tool.

4. The method of sealing a medical cartridge with a plastic closure as defined in claim 1, wherein said method includes sequentially driving a plurality of crimping tools against said tubular portion of said plastic closure adjacent said free end, each of said crimping tools having an inclined surface of a decreasing angle of inclination, thereby incrementally deforming and rolling said free end of said plastic closure into said reduced diameter neck portion without damaging said plastic closure.

5. The method of sealing a medical cartridge with a plastic closure as defined in claim 1, wherein said inclined surface of said crimping tool is stationary having a gradually decreasing angle of inclination and said method includes rotating said medical cartridge with said plastic closure assembled thereon and driving said medical cartridge with said plastic closure assembled thereon and rolling said medical cartridge and plastic closure against said gradually decreasing inclined surface.

6. The method of sealing a medical cartridge with a plastic closure as defined in claim 5, wherein said gradually decreasing inclined surface is located on an inside surface of an arcuate rail and said method including simultaneously rotating said medical cartridge with said plastic closure assembled thereon against said inclined tapered surface of said rail, said tubular collar portion of said closure adjacent said free end being incrementally deformed against said inclined surface, and said tubular portion rolling along said arcuate inside inclined surface of said rail, gradually cold forming the circumference of said free end portion of said tubular collar portion into said reduced diameter neck portion of said medical cartridge.

7. The method of sealing a medical cartridge with a plastic closure as defined in claim 1, wherein said method includes injection molding said plastic closure.

8. The method of sealing a medical cartridge with a plastic closure as defined in claim 1, wherein said medical cartridge includes an open distal end, said method including filling said barrel portion with a substance and sealing said open distal end by inserting an elastomeric stopper in said open distal end.

9. A method of sealing a medical cartridge with a polymeric closure, said medical cartridge including a tubular barrel having an open distal end and an open proximal end having a radial rim portion surrounding said open proximal end, a reduced diameter neck portion adjacent said radial rim portion, said method comprising:

molding a polymeric closure from a polymer which is sufficiently malleable to permit radial deformation, yet sufficiently rigid to retain its shape following deformation and sufficiently resistant to creep to maintain a seal between the polymeric closure and the medical cartridge following radial deformation, said closure including a generally cylindrical tubular collar portion having an internal diameter slightly greater than an outside diameter of said rim portion of said barrel and an integral radial rim portion and a central opening through said radial rim portion;

applying a pierceable stopper over said proximal end of said barrel;

telescopically receiving said tubular collar portion of said polymeric closure over said radial rim portion of said barrel with said radial rim portion of said polymeric closure overlying said pierceable stopper and said rim portion of said barrel and said tubular collar portion surrounding said rim portion and said reduced diameter neck portion of said barrel; and incrementally cold forming and rolling said tubular collar portion of said polymeric closure with a crimping tool having an inclined surface facing said tubular collar portion opposite said neck portion of said barrel and relatively rotating said barrel and said crimping tool, said inclined surface of said crimping tool incrementally cold forming and rolling said tubular collar portion of said polymeric closure radially inwardly into said reduced diameter neck portion of said barrel, permanently securing said closure on said barrel and sealing said open proximal end.

10. The method of sealing a medical cartridge with a polymeric closure as defined in claim 9, wherein said inclined surface of said tool is frustoconical and said method includes relatively rotating said crimping tool and said barrel and relatively driving said frustoconical surface against said tubular collar portion of said polymeric closure adjacent a free end of said tubular collar portion.

11. The method of sealing a medical cartridge with a polymeric closure as defined in claim 10, wherein said method includes rotating said barrel with said polymeric closure assembled thereon relative to said crimping tool and driving said tubular collar portion of said polymeric closure against said inclined surface of said crimping tool.

12. The method of sealing a medical cartridge with a polymeric closure as defined in claim 10, wherein said method includes sequentially driving a plurality of crimping tools against said tubular collar portion, said crimping tools each having an inclined surface of a decreasing angle of inclination, thereby incrementally rolling and gradually cold forming said tubular collar portion of said polymeric closure radially inwardly into said reduced diameter neck portion without damaging said polymeric closure.

13. The method of sealing a medical cartridge with a polymeric closure as defined in claim 10, wherein said inclined surface of said crimping tool is located on an inside surface of an arcuate stationary rail and said method includes driving said tubular collar portion of said polymeric closure against said inclined surface and simultaneously rotating said barrel and said tubular collar portion rolling along said arcuate inside tapered surface of said crimping tool incrementally deforming the entire circumference of said tubular portion against said rim portion of said barrel.

14. The method of sealing a medical cartridge with a polymeric closure as defined in claim 13, wherein said inclined surface of said crimping tool has a gradually decreasing angle of inclination, wherein said method includes driving said tubular collar portion of said polymeric closure against said inclined surface having a gradually decreasing angle of inclination, thereby rolling and gradually cold forming said tubular collar portion of said polymeric closure radially inwardly into said reduced diameter neck portion.

15. The method of sealing a medical cartridge with a plastic closure as defined in claim 9, wherein said method includes compressing said integral radial rim portion of said polymeric closure against said pierceable stopper to seal said polymeric closure to said stopper and substantially simultaneously incrementally rolling and cold forming said tubular collar portion of said closure into said reduced diameter neck portion of said barrel.

16. The method of sealing a medical cartridge with a polymeric closure as defined in claim 9, wherein said method includes filling said barrel with a substance and sealing said open distal end of said barrel by inserting an elastomeric stopper in said open distal end.

17. The method of sealing a medical cartridge with a polymeric closure as defined in claim 9, wherein said method includes injection molding said polymeric closure from a polymer alloy comprising a relatively malleable soft polymer and a relatively rigid polymer.

18. The method of sealing a medical cartridge with a polymeric closure as defined in claim 17, wherein said method includes co-injecting a polymer alloy including a polycarbonate and a soft malleable co-polymer.

19. A method of sealing a medical cartridge with a polymeric closure, said medical cartridge including a barrel having an open distal end and an open proximal end, including a radial rim portion surrounding said open proximal end and a reduced diameter neck portion adjacent said rim portion and an elastomeric septum received over said open proximal end of said barrel including a rim portion overlying said rim portion of said barrel, said method comprising the following steps:

forming a polymeric closure including a generally cylindrical tubular collar portion having an internal diameter generally equal to or slightly greater than an outside diameter of said rim portion of said barrel and an integral radial rim portion having a central opening from a polymer which is sufficiently malleable to permit radial deformation, yet sufficiently rigid and resistant to creep to retain its shape following deformation;

telescopically receiving said tubular collar portion of said polymeric closure over said radial rim portion of said barrel and said rim portion of said elastomeric septum with said rim portion of said polymeric closure overlying said rim portion of said elastomeric septum and said tubular collar portion surrounding said rim portion and said reduced diameter neck portion of said barrel; and compressing said rim portion of said polymeric closure against said rim portion of said elastomeric septum, and incrementally rolling and gradually cold forming said tubular collar portion of said polymeric closure against an inclined surface of a crimping tool having a decreasing angle of inclination opposite said neck portion of said barrel and relatively rotating said barrel against said inclined surface of said crimping tool, thereby incrementally rolling and gradually cold forming said tubular collar portion of said polymeric closure radially inwardly into said reduced diameter neck portion of said barrel, permanently securing said closure on said barrel and sealing said open proximal end of said barrel.

20. The method of sealing a medical cartridge with a polymeric closure as defined in claim 19, wherein said method includes sequentially driving a plurality of crimping tools against said tubular collar portion of said polymeric closure each having an inclined surface of a different decreasing angles of inclination, thereby rolling and gradually cold forming said tubular collar portion of said polymeric closure into said reduced diameter neck portion of said barrel.

21. The method of sealing a medical cartridge with a polymeric closure as defined in claim 19, wherein said method includes rolling and gradually cold forming said tubular collar portion of said polymeric closure by driving said barrel and polymeric closure against a stationary crimping tool having a gradually decreasing angle of inclination and simultaneously rotating said barrel and polymeric closure while maintaining compression of said radial rim portion of said polymeric closure against said rim portion of said elastomeric septum.

22. The method of sealing a medical cartridge with a polymeric closure as defined in claim 19, wherein said method further includes filling said barrel with a substance and sealing said open distal end by inserting an elastomeric stopper in said open distal end.

* * * * *